United States Patent [19]

Moore et al.

[11] Patent Number: 5,531,700
[45] Date of Patent: Jul. 2, 1996

[54] CONVERTIBLE TIP CATHETERS AND SHEATHS

[75] Inventors: Thomas C. Moore, Santa Clara; Yue-Teh Jang, Fremont, both of Calif.

[73] Assignee: Cardiovascular Imaging Systems, Inc., Sunnyvale, Calif.

[21] Appl. No.: 282,864

[22] Filed: Jul. 29, 1994

[51] Int. Cl.$^6$ .................................................. A61M 25/09
[52] U.S. Cl. .............................. 604/164; 604/96; 604/280
[58] Field of Search ........................................ 604/164, 280, 604/281, 43, 96

[56] References Cited

U.S. PATENT DOCUMENTS

| | | | |
|---|---|---|---|
| 1,879,249 | 9/1932 | Honsaker | 604/280 |
| 1,968,997 | 8/1934 | Drucker | 604/164 |
| 2,116,083 | 5/1938 | Rusch | 604/280 |
| 3,828,767 | 8/1974 | Spiroff | 604/280 |
| 4,385,631 | 5/1983 | Uthmann | 604/43 |
| 4,552,554 | 11/1985 | Gould et al. . | |
| 4,692,141 | 9/1987 | Mahurkar | 604/43 |
| 4,824,435 | 4/1989 | Giesy et al. . | |
| 4,863,441 | 9/1989 | Lindsay et al. | 604/280 |
| 4,932,413 | 6/1990 | Shockey et al. . | |
| 4,951,677 | 8/1990 | Crowley et al. . | |
| 5,024,234 | 6/1991 | Leary et al. . | |
| 5,069,673 | 12/1991 | Shwab | 604/280 |
| 5,154,725 | 10/1992 | Leopold | 604/96 |
| 5,195,962 | 3/1993 | Martin et al. | 604/164 |
| 5,201,316 | 4/1993 | Pomeranz et al. . | |
| 5,203,338 | 4/1993 | Jang . | |
| 5,207,655 | 5/1993 | Sheridan | 604/96 |
| 5,215,527 | 6/1993 | Beck et al. | 604/43 |
| 5,215,540 | 6/1993 | Anderhub | 604/281 |
| 5,242,387 | 9/1993 | Loughlin | 604/43 |
| 5,273,527 | 12/1993 | Schatz et al. | 604/164 |
| 5,300,048 | 4/1994 | Drewes, Jr. et al. | 604/280 |
| B14,762,129 | 7/1991 | Bonzel . | |

FOREIGN PATENT DOCUMENTS 07323  2/1994  WIPO .

OTHER PUBLICATIONS

Intertherapy "Product Development Update," InterTherapy, Costa Mesa, California, Fall 1990.

*Primary Examiner*—Paul J. Hirsch
*Attorney, Agent, or Firm*—Townsend and Townsend and Crew

[57] ABSTRACT

A catheter is provided having a catheter body with a proximal end and a distal end. The catheter body has a proximal region having a first diameter and a distal region having a single lumen and a second diameter which is less than a first diameter. A distal guide wire exit port is disposed in the distal region of the catheter body within about 5 cm of the distal end. This allows the catheter to be used as a short lumen rapid exchange catheter. The catheter can also be provided with a proximal guide wire exit port in the proximal region so that the catheter can also be used as a long lumen rapid exchange catheter.

26 Claims, 8 Drawing Sheets

FIG_1

FIG_1A

FIG_2

FIG_3

FIG_3A

FIG_3B

FIG_4

FIG_5

FIG_6

FIG_7

FIG_8

FIG_9

FIG_10

FIG_11

FIG_12

FIG_13

FIG_14

CONVERTIBLE TIP CATHETERS AND SHEATHS

BACKGROUND OF THE INVENTION

1. Field of the Invention

The present invention relates generally to vascular catheters, and in particular to improved vascular catheters and methods for their insertion into the vascular anatomy over guide wires.

Atherosclerosis is a common human ailment arising from deposition of fatty-like substances, referred to as atheroma or plaque, on the walls of blood vessels. Such deposits occur both in the peripheral blood vessels, which feed the limbs of the body, and the coronary vessels, which feed the heart. When deposits accumulate in localized regions of a blood vessel, narrowing of the vascular lumen, referred to as stenosis occurs. Blood flow is restricted and the person's health is at serious risk.

Numerous approaches for opening such stenosed regions are known. Of particular interest to the present invention are approaches which introduce diagnostic or therapeutic devices into the vascular anatomy through a catheter or a sheath. For instance, one known approach is balloon angioplasty where a balloon-tipped catheter is used to dilate a stenosed region (optionally in combination with a stent for maintaining patency). In another approach referred to as atherectomy, a blade, cutting element or other abrasive element, is introduced through a catheter or sheath and is used to remove the atheroma or plaque. Other approaches include spark gap reduction where an electric spark burns through the atheroma or plaque, and laser angioplasty where laser energy is used to ablate at least a portion of the atheroma or plaque. With any one of these approaches, it is often desirable to obtain an image of the interior of the blood vessel at the region to be treated. Catheters having imaging elements such as ultrasonic transducers are now gaining widespread acceptance for producing such images.

Ultrasonic imaging catheters will often include an imaging core comprising ultrasonic imaging transducer or reflective element mounted on a rotatable drive shaft disposed within a flexible catheter body. The transducer, reflective element or both, can be rotated within the catheter body to direct an ultrasonic signal generally outward in order to scan the interior of the blood vessel wall. High resolution images revealing information concerning the extent and nature of the stenotic material can thus be produced.

During diagnostic, imaging, and interventional vascular procedures, it is often desirable to "exchange" one catheter for another. By "exchange" it is meant that one catheter is withdrawn from the vascular system and another catheter is introduced to the vascular system. In order to maintain distal access, the exchange will usually be performed over a guide wire which is left in place to facilitate both catheter withdrawal and reintroduction of the new catheter.

Of particular interest to the present invention are "rapid exchange" catheter designs. Unlike earlier catheter designs (referred to hereinafter as "conventional over-the-wire" designs) where the entire catheter body was inserted over the guide wire, the rapid exchange catheters have a guide wire lumen that does not extend the full length of the catheter. Rather, the guide wire lumen extends only from the distal tip to a side "exit" port which terminates a short distance proximal of the distal tip. Two rapid exchange catheter designs which are of particular interest to the present invention are long lumen rapid exchange designs and short lumen rapid exchange designs (the latter sometimes being referred to as "monorail" designs).

In the case of long lumen rapid exchange catheters, the side port through which the guide wire exits will typically be 10 cm or more from the distal tip of the catheter. In a particular type of long lumen rapid exchange catheters, referred to as a common lumen rapid exchange catheter or sheath, the catheter body includes a working lumen in addition to the guide wire lumen. These two lumens are disposed in a proximal region of the catheter and are in communication with a common lumen at a distal region of the catheter. The guide wire is introduced through the common lumen and advanced into the proximal guide wire lumen when inserting the catheter into a patient. The relatively long engagement of the guide wire with common lumen and the guide wire lumen allows the distal end of the catheter to more easily be passed through tortuous regions of the vascular anatomy. This is often referred to as providing the catheter with good "trackability".

Another advantage of common long lumen rapid exchange catheters is that once the catheter is in the desired region of the vascular anatomy, the guide wire can be withdrawn from the vessel, and stored in the guide wire lumen just proximal to the common lumen. A diagnostic or therapeutic device can then be advanced from the working lumen and into the common lumen without being obstructed by the guide wire. This is especially desirable when an imaging core is advanced into the common lumen so that imaging can occur without obstruction from the guide wire.

A further advantage of common long lumen rapid exchange designs is that the common lumen of the catheter serves as a protector for the imaging core. This is of particular importance when imaging an area of a vessel displaced by a stent. The common lumen of the catheter or sheath protects the imaging core from unexpected collapse of the stent.

Common long lumen rapid exchange catheters are also advantageous in that the guide wire can easily be readvanced from the stored location in the guide wire lumen, through the common lumen, and into the vessel. Once the guide wire is readvanced into the vessel, the catheter can be repositioned or removed while the guide wire protects the vessel. In still another advantage, the long engagement with the guide wire prevents buckling and prolapse of the guide wire when removing the catheter from the vessel.

Drawbacks to common long lumen rapid exchange designs include the possibility of damaging the artery with the distal tip of the catheter when the guide wire is removed from the distal region and stored in the guide wire lumen. Without the guide wire to secure the catheter in the vessel, the distal tip of the catheter can accidently be advanced causing damage to the artery. Another problem experienced with long lumen rapid exchange catheters is that, in emergency situations, some physicians will withdraw the entire catheter from the patient (along with the guide wire), instead of readvancing the guide wire from the guide wire lumen and into the vessel, and then removing the catheter with the guide wire still in place.

Short lumen rapid exchange catheter designs generally employ a much shorter guide wire lumen at the distal end of the catheter, typically in the range from about 1 cm to 4 cm. Further, unlike the long lumen rapid exchange catheters, the guide wire lumen is not disposed within the proximal region of the catheter body. Hence, the guide wire is usually not removed from the vessel when using short lumen rapid exchange designs.

Once the short lumen rapid exchange catheter is positioned in the artery, an interventional, imaging, or diagnostic component of a catheter may then be disposed proximally through a separate access lumen in the short lumen rapid exchange catheter body and up to the guide wire lumen. Alternatively, a fixed interventional element such as an angioplasty balloon may be disposed on the catheter body proximal to the short guide wire lumen. Since a majority of the length of the guide wire is not stored in the catheter body, the cross sectional area of the catheter can be made smaller than most long lumen rapid exchange designs while still providing space for introducing other devices. As previously described, the short lumen rapid exchange design also allows the guide wire to remain in place in the vessel. This allows for easy removal of the catheter and the insertion of another catheter along the guide wire.

While such short lumen rapid exchange designs have proven to be very valuable, particularly for introduction of catheters to very small blood vessels, the small engagement of the guide wire with the catheter has proven problematic. For instance, short lumen rapid exchange designs have poor trackability. Further, buckling or prolapse of the guide wire can occur when removing the catheter from the vessel.

For these reasons, two or more different catheters can be introduced during a single operation. This can be inconvenient to a surgeon who may be required to remove a variety of different catheters from their packages and then introduce these into the patient. Furthermore, the use of several different catheter designs can increase the cost of the operation.

It would thus be desirable to provide catheters and sheaths incorporating features of both a long lumen rapid exchange design and a short lumen rapid exchange design for use in vascular procedures. For instance, it would be desirable to employ the long lumen rapid exchange design in situations where trackability is required and the short lumen rapid exchange catheter to treat very small vessels.

2. Description of the Background Art

Vascular ultrasonic imaging catheters having rapid exchange designs are described in U.S. Pat. Nos. 5,201,316; 5,024,234; and 4,951,677. Catheter sheaths having guide wire side ports near their distal ends are described in U.S. Pat. Nos. 4,932,413; 4,824,435; and 4,552,554. A short lumen rapid exchange balloon dilation catheter is described in U.S. Pat. No. B 1 4,762,129. An ultrasonic imaging catheter having a common distal lumen is described in U.S. Pat. No. 5,203,338. A monorail sheath catheter usable with an ultrasonic imaging core was described in a Product Development Update of Intertherapy, Costa Mesa, Cal, dated: Fall 1990. A catheter having a guide wire lumen with a slidable sleeve is described in PCT International Application No. PCT/US93/07323.

SUMMARY OF THE INVENTION

According to the invention, a vascular catheter comprises a catheter body having a proximal end and a distal end. The catheter body further includes a proximal region having at least one lumen and a first outside diameter and a distal region having a single lumen and a second outside diameter which is less than the first diameter. A distal guide wire exit port is disposed in the distal region of the catheter body within 5 cm of distal end. The distal guide wire exit port provides the vascular catheter with a short lumen rapid exchange catheter design, while the proximal lumen provides for conventional over-the-wire exchange, long lumen rapid exchange, or both. In a preferred aspect, a proximal guide wire exit port is disposed in the proximal region within 10 cm to 20 cm of a proximal end of the distal region. The proximal guide wire exit port provides the vascular catheter with a long lumen rapid exchange design.

In one particular aspect, the vascular catheter includes a transition region near the distal guide wire exit port for assisting in the advancement of the guide wire through the distal guide wire exit port. In an exemplary aspect, the transition region includes a guide within the single lumen in the distal region. In a further aspect, the guide includes an inclined member integrally formed with the catheter body and inclined toward the distal guide wire exit port. As the guide wire passes along the inclined member, the guide wire will be directed toward the exit port. Preferably, the proximal region has an outside diameter in the range from 1.2 mm to 2 mm and the distal region has an outside diameter in the range from 0.6 mm to 1.6 mm.

In yet another particular aspect, at least a portion of the distal region that is near the distal guide wire exit port is constructed of a material that is softer than material used to construct the catheter body just proximal to the distal guide wire exit port. This provides a preferential bending scheme so that when the distal end of the catheter is bent, the catheter body will bend near the distal guide wire exit port to more easily allow the guide wire to exit from the port.

In an exemplary embodiment, a vascular catheter is provided having a catheter body with a proximal end and a distal end. The catheter body has a proximal region having at least two lumens and a distal region having a single lumen which is connected to and in communication with both the lumens in the proximal region. A distal guide wire exit port is disposed in the distal region of the catheter body within 5 cm of the distal end. The distal guide wire exit port allows the catheter to function as a short lumen rapid exchange catheter. In a preferred aspect, a proximal guide wire exit port is disposed in the proximal region of the catheter body within 10 cm to 20 cm of a proximal end of the distal region. The proximal guide wire exit port allows the catheter to function as a long lumen rapid exchange catheter.

In one aspect of this embodiment, the catheter includes a transition region near the distal guide wire exit port for assisting in the advancement of the guide wire through the distal guide wire exit port. In an exemplary aspect, the transition region includes a guide within the single lumen in the distal region. The guide assists in directing the advancing guide wire towards the exit port.

In still a further aspect, the proximal region has an outside diameter in the range from 1.2 mm to 2 mm and the distal region has an outside diameter in the range from 0.6 mm to 1.6 mm. In another aspect, one of the two lumens in the proximal region is preferably a guide wire lumen having an inside diameter in the range from 0.3 mm to 0.6 mm. Preferably, the proximal guide wire exit port is in communication with the guide wire lumen. In still a further aspect, the distal region has a cross sectional area which is less than the cross sectional area of the proximal region.

The present invention further provides a method for inserting a catheter over a guide wire. The method includes providing a catheter having a catheter body with a proximal end and a distal end. The catheter body has a proximal region having a first outside diameter and at least one lumen and a distal region having a single lumen and a second outside diameter which is less than the first diameter. A distal guide wire exit port is disposed in the distal region of the catheter body within 5 cm of the distal end. The single lumen distal region of the catheter body is advanced over the guide wire. The guide wire is then selectively directed either (1) outward through the distal guide wire exit port or (2) into the proximal region of the catheter. In another aspect of the method, the guide wire is directed (1) through the proximal guide wire exit port in the manner of a long lumen rapid exchange catheter or (2) out of the catheter body through the proximal end in the manner of a conventional over-the-wire catheter.

In still a further aspect, a working element is introduced and/or manipulated through the proximal region, preferably through a working lumen. In yet another aspect, a guide wire is directed through a guide wire lumen in the proximal region.

In another aspect of the method, the guide wire is withdrawn from the distal end and perfusion is delivered through a plurality of perfusion ports disposed in the distal region.

In a preferable aspect, the catheter body is bent near the distal guide wire exit port to assist in guiding the guide wire through the exit port.

DETAILED DESCRIPTION OF THE SPECIFIC EMBODIMENT

The present invention provides improved catheters and catheter sheaths. Both the catheters and catheter sheaths of the present invention include a catheter body having a proximal end and a distal end. The catheters differ from catheter sheaths in that catheters have a proximal hub and include an interventional or diagnostic component, while catheter sheaths include only a hemostasis valve and receive other devices (including other catheters). The catheter body further includes a proximal region and a distal region. Usually, although not required, the distal region will have a cross sectional area smaller than the cross sectional area of the proximal region. The catheter or sheath is configured to receive other diagnostic or interventional devices. These devices are inserted through the proximal end of the catheter or sheath and can be held in the proximal region. When needed during a procedure, these devices can be advanced from the proximal region and into the single lumen of the distal region or further through the distal end of the catheter body.

Typical diagnostic or interventional devices that can be introduced through the catheter include catheters (such as balloon angioplasty catheters) or can include working shafts having a work element at or near their distal end. The work element will usually be an ultrasonic transducer useful for intervascular imaging, but may also comprise a variety of other diagnostic or interventional elements such a cutting elements, abrasive heads, and the like. The catheter body itself may have interventional components incorporated therein, such as angioplasty balloons as described in copending U.S. Pat. Ser No. 08/100,642 (Attorney Docket No. 12553-36-1). The construction and use of these types of diagnostic and interventional devices is now well know and well described in medical literature. The following discussion will be directed to the introduction of the catheter sheath along a guide wire and into the vascular anatomy, rather than the particular diagnostic or therapeutic devices that may be introduced therethrough.

Catheter bodies for constructing the catheters and sheaths of the present invention will usually be formed by extrusion of an organic polymer, typically a thermoplastic such as polyethylene, polyethyleneterephthalate (PET), polyurethane, polyvinylchloride (PVC), nylon and the like. The catheter body will usually be unreinforced, but optionally may be reinforced with metal wires, metal braided cables, metal coils, and the like. The catheter body will typically have a length in the range from about 60 cm to 200 cm, usually being from 60 cm to 110 cm for use in the peripheral arteries and from 90 cm to 150 cm for use in the coronary arteries. The diameter will usually be about 0.33 mm or larger, more usually being from 1 mm to 2 mm. The catheter constructions of the present invention are particularly useful with very small diameter catheters below 1.5 mm, particularly below 1.2 mm.

The proximal region will usually have a length in the range from about 110 cm to 125 cm and an outside diameter in the range from 1.2 mm to 2 mm. The distal region will usually have a length in the range from about 5 cm to 20 cm and an outside diameter in the range from 0.6 mm to 1.6 mm.

Disposed in the distal region of the catheter body is a distal guide wire exit port. The distal guide wire exit port is located within about 5 cm of the distal end. The distal guide wire exit port provides the catheter or sheath with a short lumen rapid exchange configuration. The catheter or sheath may be inserted into the vascular anatomy along a guide wire by directing the distal end of the catheter body over the guide wire and directing the guide wire through the distal region and out the distal guide wire exit port. Alternatively, the guide wire can be advanced further through the catheter body and beyond the distal guide wire port as described hereinafter.

In another aspect of the invention, a proximal guide wire exit port is disposed in the proximal region within about 10 cm to 20 cm of a proximal end of the distal region. More typically, the proximal guide wire exit port will be disposed in the proximal region within about 10 cm to 15 cm of the proximal end of the distal region. The proximal guide wire exit port provides the catheter or sheath with a long lumen rapid exchange configuration. With this configuration, the catheter or sheath is inserted into the vascular anatomy by directing the guide wire through the distal region and into the proximal region where the guide wire exits the proximal region from the proximal guide wire exit port. Alternatively, the guide wire can be further directed through the entire proximal region where it will exit through the proximal end of the catheter body in a conventional over-the-wire manner.

To assist in directing the guide wire through the exit ports, a transition region in the catheter body can be provided. The transition region will typically include guide within the catheter body that will assist in directing the guide wire toward the exit port. The guide will preferably be an inclined member that is integrally formed within the single lumen of the distal region with an incline toward the exit port. The guide in the transition region will not prevent the guide wire from further advancement through the catheter body if it is desired to by-pass the exit port.

Figure 1:
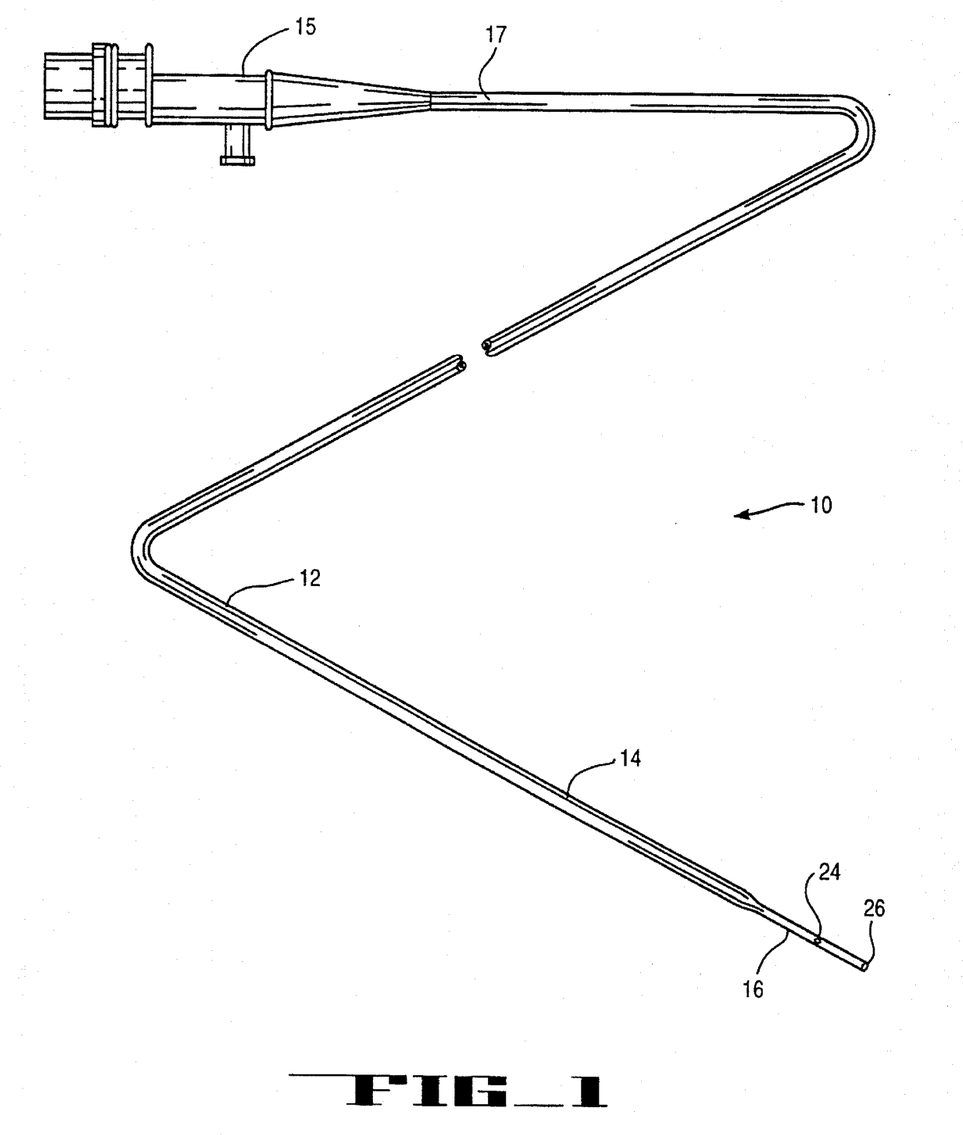
FIGS. 1 and 1A illustrate an embodiment of a vascular catheter having a distal guide wire exit port according to the present invention.
Figure 1A:
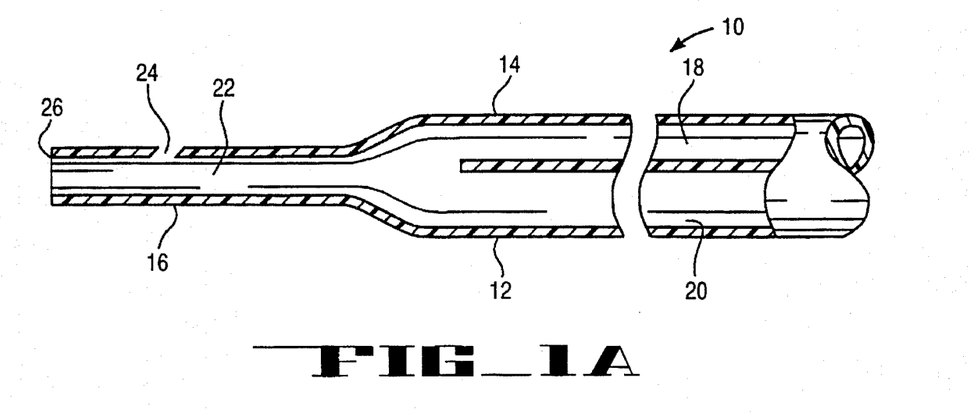

Referring now to FIGS. 1 and 1A, an embodiment of a vascular catheter 10 is shown. The catheter 10 includes a catheter body 12 having a proximal region 14 and a distal region 16. As shown in FIG. 1, a proximal housing 15 is provided at a proximal end 17 of the catheter body 12. As shown in FIG. 1A, the proximal region further includes two lumens 18, 20, where lumen 18 is typically used as a guide wire lumen and lumen 20 as a working lumen. The distal region includes a single lumen 22 that is connected to and in communication with the lumens 18, 20 in the proximal region 14. Usually, the cross sectional area of the proximal region 14 is larger than the cross sectional area of the distal region 16. Construction of a catheter having a single lumen at a distal region and two lumens at a proximal region is described in U.S. Pat. No. 5,203,338, the disclosure of which is hereby incorporated by reference.

Disposed in the distal region 16 is a distal guide wire exit port 24. The distal guide wire exit port will usually be located within about 1 cm to 10 cm of the distal end 26, and preferably within about 1 cm to 5 cm of the distal end 26. After a guide wire is passed through a distal end 26 of the catheter body 12, the guide wire can exit the distal region 16 through the distal guide wire exit port 24. This configuration provides the catheter 10 with a short lumen rapid exchange design.

Figure 2:
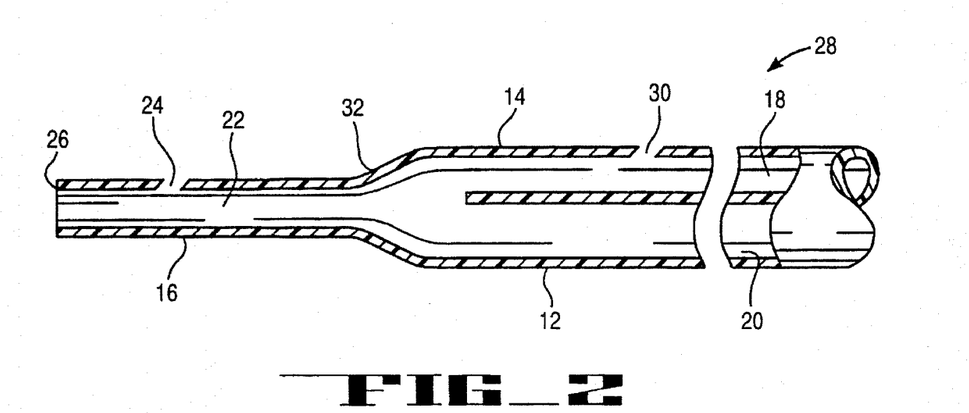
FIG. 2. illustrates an exemplary catheter design having both a distal guide wire exit port and a proximal guide wire exit port according to the present invention.

Referring to FIG. 2, an exemplary embodiment of a vascular catheter 28 is shown. The catheter 28 is essentially identical to the catheter 10 of FIG. 1 except that catheter 28 is further provided with a proximal guide wire exit port 30. For convenience of discussion, FIG. 2 will be described using the same reference numerals used in FIG. 1. The proximal guide wire exit port 30 will usually be located within about 10 cm to 20 cm of a proximal end 32 of the distal region 16, and preferably within about 10 cm to about 15 cm of the proximal end 32 of the distal region 16. The distal guide wire exit port 24 and the proximal guide wire exit port 30 provide the catheter 28 with both a short lumen rapid exchange design and a long lumen rapid exchange design. A guide wire can be advanced through the distal end 26 and into the single lumen 22. The guide wire can then be advanced either through the distal guide wire exit port 24 (as previously described) or further along the single lumen 22 and into the proximal region 14. The guide wire can then be directed through the guide wire lumen 18 and through either the proximal guide wire exit port 30 or further through the lumen 18.

One advantage in providing the distal guide wire exit port 24 is that the catheter 10 or 28 can easily be removed from the vascular anatomy over the guide wire because of the short region of engagement with the guide wire. The short engagement with the guide wire also allows a working element (such as an ultrasonic imaging transducer) to be advanced into the distal region 22 with the guide wire in place.

If trackability is a concern, making it less desirable to use the distal guide wire exit port 24, the proximal guide wire exit port 30 of catheter 28 can be employed. This provides a longer area of engagement with the guide wire so that the catheter 28 can be passed through tortuous regions of the vascular anatomy. A further advantage of employing port 30 is that the catheter 28 can be removed from the vascular anatomy without having the guide wire buckling or experiencing prolapse due to the long engagement with the guide wire. In still a further advantage, once the catheter 28 is in place, the guide wire can be retracted from the single lumen 22 and into the guide wire lumen 18 for storage. Therapeutic or diagnostic devices can then be introduced into the single lumen 22 through lumen 20. If the guide wire subsequently needs to be readvanced into the artery, the therapeutic or diagnostic device can be removed to the proximal region 14 and the guide wire readvanced into the single lumen 22 and out the distal end 26.

Another advantage of catheter 28 is that it can be reused if another region in the vascular anatomy needs treatment or diagnosis. To reuse catheter 28, the catheter is simply withdrawn from the patient and the guide wire is introduced into the new region. The catheter 28 is then reinserted over the guide wire and advanced into the vascular anatomy. Since the catheter 28 has both a distal guide wire exit port 24 and a proximal guide wire exit port 30, the catheter 28 can be reinserted over the repositioned guide wire as either a short lumen rapid exchange catheter or a long lumen rapid exchange catheter by using either the distal guide wire exit port 24 or the proximal guide wire exit port 30, respectively. Alternatively, the guide wire can be advanced entirely through the guide wire lumen 18 in a conventional over-the-wire manner.

In yet another advantage, use of the distal guide wire exit port 24 allows the guide wire to remain in the vessel while diagnosis or treatment occurs. Maintenance of the guide wire in the vessel helps to prevent the distal end 26 from being advanced further into the vessel which could harm the vessel.

Figure 3:
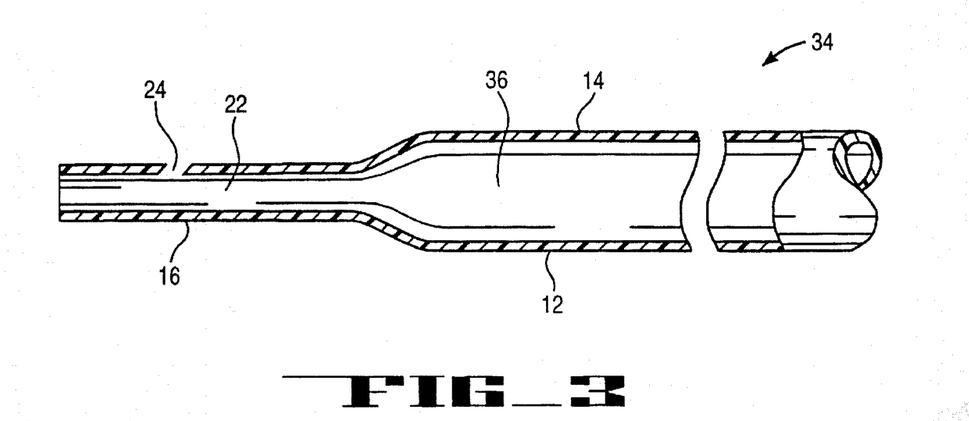
FIG. 3 illustrates an embodiment of a vascular catheter having a distal guide wire exit port and having only a single lumen.
Figure 3A:
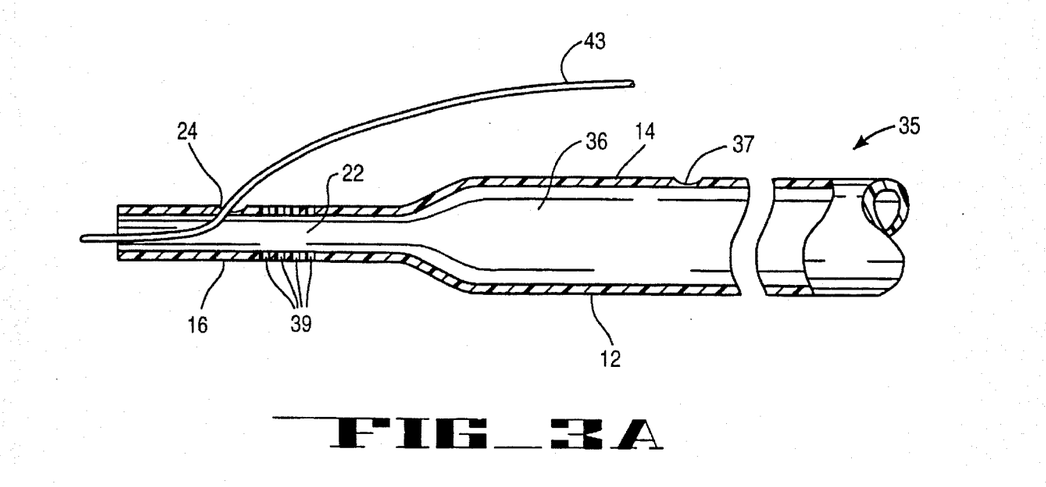
FIGS. 3A and 3B illustrate the catheter of FIG. 3 with a proximal guide wire exit port and a plurality of perfusion ports.
Figure 3B:
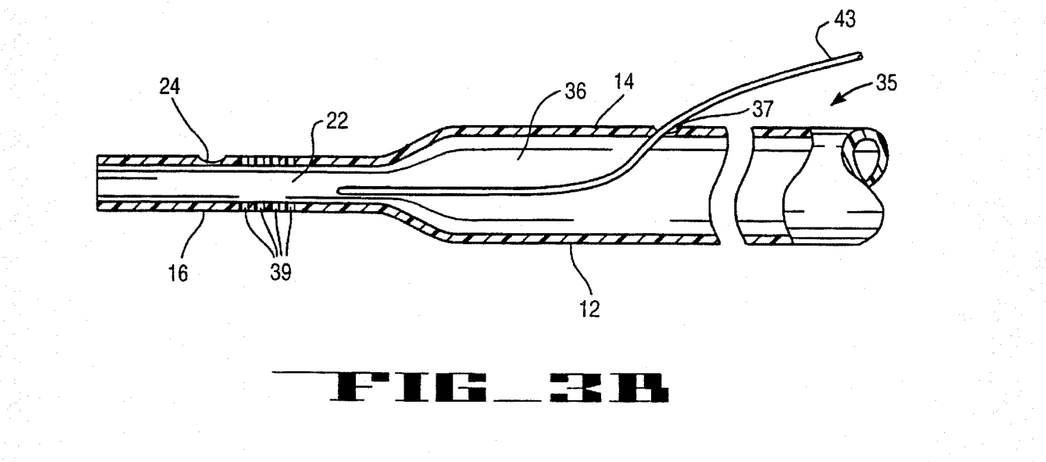

Shown in FIG. 3 is a single lumen catheter 34 having a distal guide wire exit port 24. The single lumen catheter 34 is essentially identical to the catheter 10 of FIG. 1 except that the proximal region 14 has only a single lumen. The distal guide wire exit port 24 provides the catheter 34 with a short lumen rapid exchange configuration as previously described. However, the proximal region 14 has only a single lumen 36 that is connected to and in communication with the single lumen 22 in the proximal region 14. This provides the advantages of lower proximal profile in the case of a perfusion catheter 35 as shown in FIGS. 3A and 3B. The perfusion catheter 35 is essentially identical to the single lumen catheter 34, but further includes a proximal guide wire exit port 37 and a plurality of perfusion ports 39 for injecting perfusion through the side of the catheter body 12. The perfusion can be injected into the artery with a guide wire 43 being directed through either the distal guide wire exit port 24 (as shown in FIG. 3A) or the proximal guide wire exit port 37 (as shown in FIG. 3B). To allow for easier injection of the perfusion when using the proximal guide wire exit port 37, the guide wire 43 can be withdrawn from the distal region 16 and into the proximal region 14.

Although not shown, the single lumen catheter 34 can also be provided with a proximal guide wire exit port 30 as previously described in connection with FIG. 2. Hence, the single lumen catheter 34 can be configured either as a short lumen rapid exchange catheter or a long lumen rapid exchange catheter.

Figure 4:
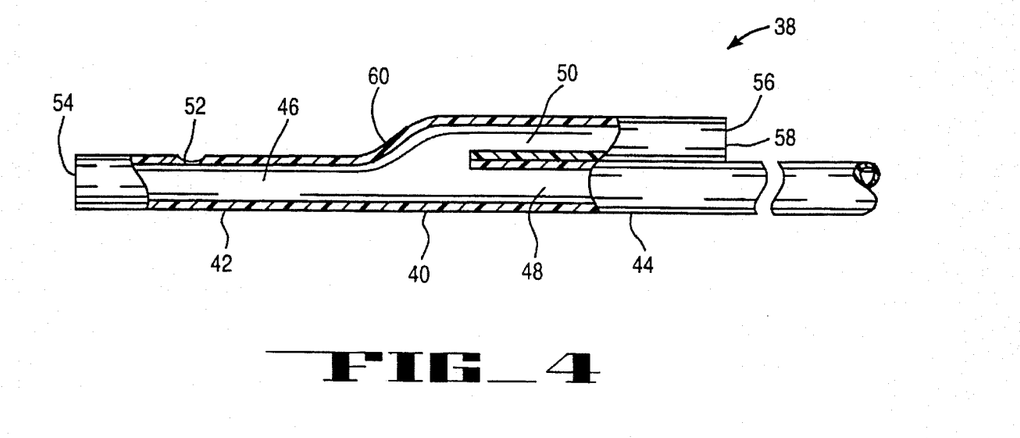
FIG. 4 illustrates an alternative embodiment of a catheter design having both a distal guide wire exit port and a proximal guide wire exit port according to the present invention.

In FIG. 4, an alternative embodiment of a rapid exchange catheter 38 is shown. The catheter 38 has both a short lumen rapid exchange configuration and a long lumen rapid exchange configuration. The catheter 38 includes a catheter body 40 having a distal region 42 and a proximal region 44. The distal region has a single lumen 46 while the proximal region 44 has a central lumen 48 and a shortened guide wire lumen 50. Disposed in the catheter body 40 at the distal region 42 is a distal guide wire exit port 52. The exit port 52 will usually be located within about 1 cm to 10 cm of a distal end 54, more preferably within about 1 cm to 5 cm of the distal end 54. A proximal guide wire exit port 56 is disposed at a distal end 58 of the guide wire lumen 50. The proximal guide wire exit port 56 will preferably be disposed within about 10 cm to 20 cm of a proximal end 60 of the distal region 42. However, the proximal guide wire exit port 56 can be located anywhere along the proximal region 44 by simply extending the length of the guide wire lumen 50. By configuring the guide wire lumen 50 in this manner, a guide wire exiting through the proximal guide wire exit port 56 is directed along the catheter body 40. The distal guide wire exit port 52 provides the catheter 38 with a short lumen rapid exchange design while the proximal guide wire exit port 56 provides the catheter 38 with a long lumen rapid exchange design.

Figure 5:
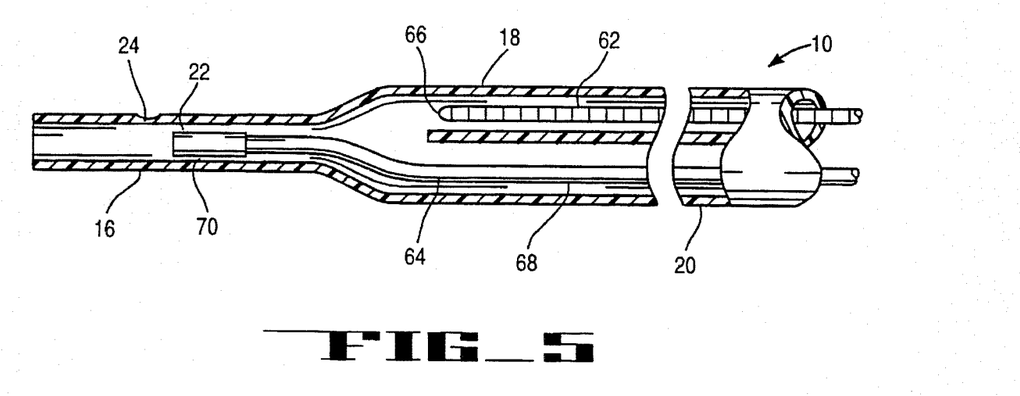
FIG. 5 illustrates the catheter of FIG. 1 having a guide wire in the guide wire lumen and a imaging transducer directed through the working lumen.

Referring to FIG. 5, the catheter 10 of FIG. 1 will be described in context with a guide wire 62 and an ultrasonic imaging core 64. As shown in FIG. 5, the guide wire 62 has by-passed the distal guide wire exit port 24 and is stored within the guide wire lumen 18. Once the guide wire 18 is within the lumen 18, the ultrasonic imaging core 64 is advanced from the lumen 20 and into the single lumen 22 of the distal region 16.

The ultrasonic imaging core 64 includes a drive shaft 68 connected to an imaging transducer 70 as described in U.S. Pat. No. 5,203,338, the disclosure of which has previously been incorporated by reference. The drive shaft 68 rotates the transducer 70 to provide an image of the desired region of the artery.

Although not shown, the catheter 10 can alternatively be provided with a proximal guide wire exit port as previously described in FIG. 2. The distal end of the guide wire can be directed through this exit port so that only a proximal region of the guide wire 62 is stored in the guide wire lumen 18. Since the guide wire 62 can still be retracted into the guide wire lumen 18 with this configuration, the single lumen 22 is available to receive the transducer 70.

Figure 6:
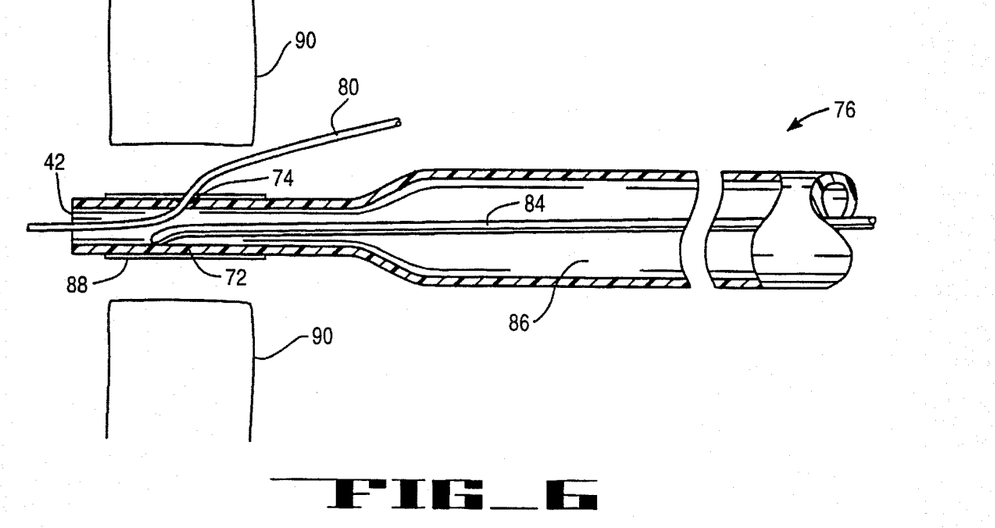
FIG. 6 illustrates an exemplary method for constructing a vascular catheter having a distal guide wire lumen.
Figure 7:
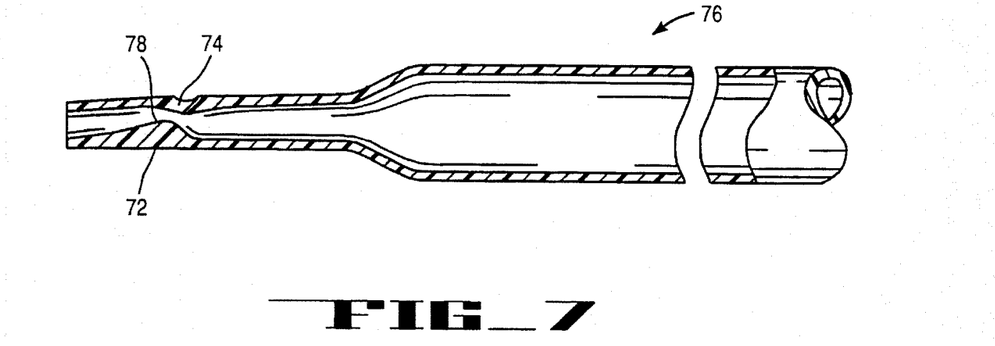
FIG. 7 illustrates a transition region near a distal guide wire exit port formed according to the method shown in FIG. 6.

Referring to FIGS. 6 and 7, catheters according to the present invention can be provided with a transition region 72 (see FIG. 7) for assisting in the exit of the guide wire through a guide wire exit port 74. Although described in the context of a single lumen catheter 76, the transition region 72 can equally be formed in the embodiments described in Figs. 1, 1A, 2, and 4. The transition region 72 includes a guide 78 that assists in directing the guide wire towards the guide wire exit port 74. As described hereinafter, the guide 78 is an inclined member that is integrally formed with the catheter body and inclines toward the exit port 74. As a guide wire passes along the guide 78, the guide wire will be directed by the guide 78 toward the exit port 74.

To form the guide 78, a guide wire mandrel 80 is positioned through the guide wire exit port 74 and out a distal end 82. A central lumen mandrel 84 is then directed through a central lumen 86 to a point just proximal to the guide wire mandrel 80. A shrink tube 88 such as polyethylene, polytetrafluoroethylene, or silicon is then placed around the catheter near the transition region 72 and heat is supplied from a heat source 90. The heat causes the shrink tube 88 to contract while causing the material in the transition region 72 to soften and/or melt. The contraction of the shrink tube then causes the material to form around the mandrels 80, 84 and to produce the guide 78. When cooled, the mandrels 80, 84 are removed to produce the transition region 72 shown in FIG. 7.

Figure 8:
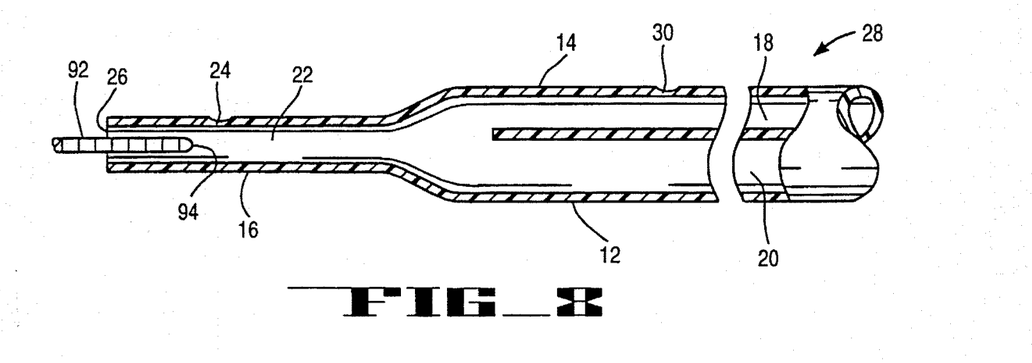
FIGS. 8–12 illustrate exemplary methods for inserting a guide wire through a distal end of a vascular catheter having both a distal guide wire exit port and a proximal guide wire exit port.
Figure 9:
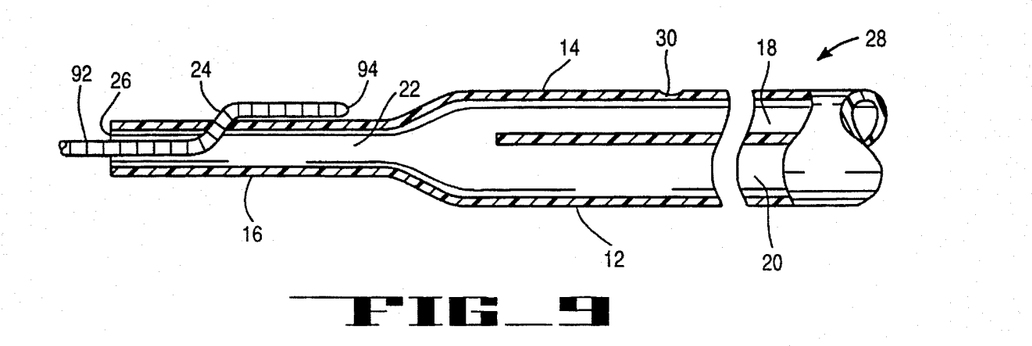
Figure 10:
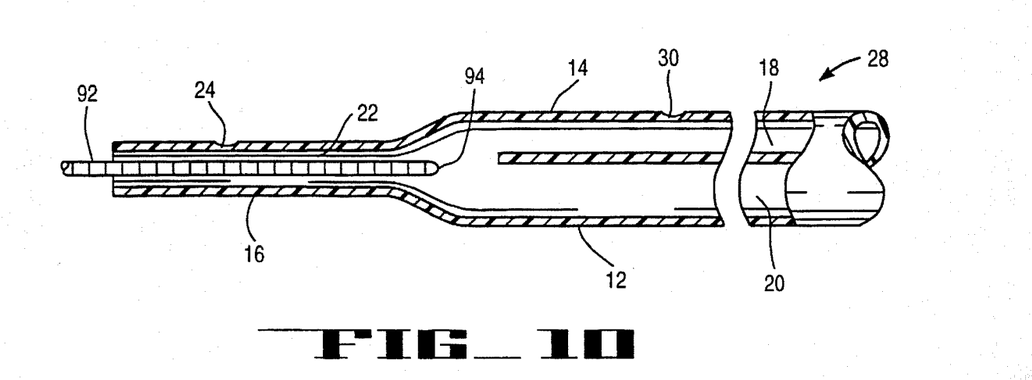
Figure 11:
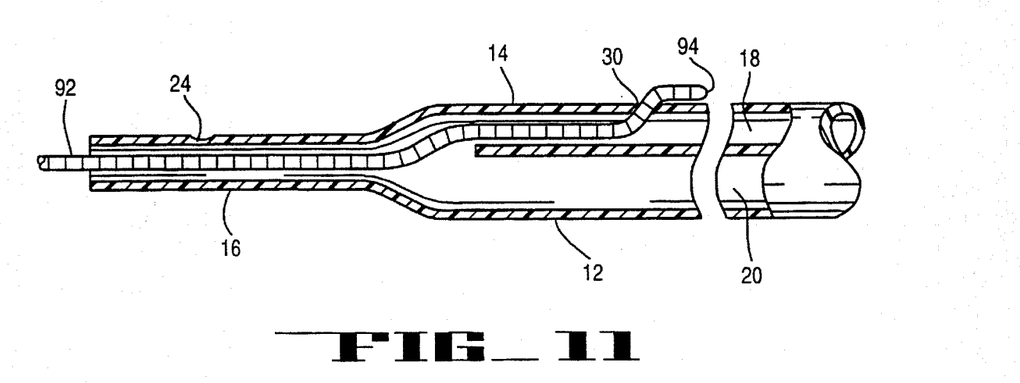
Figure 12:
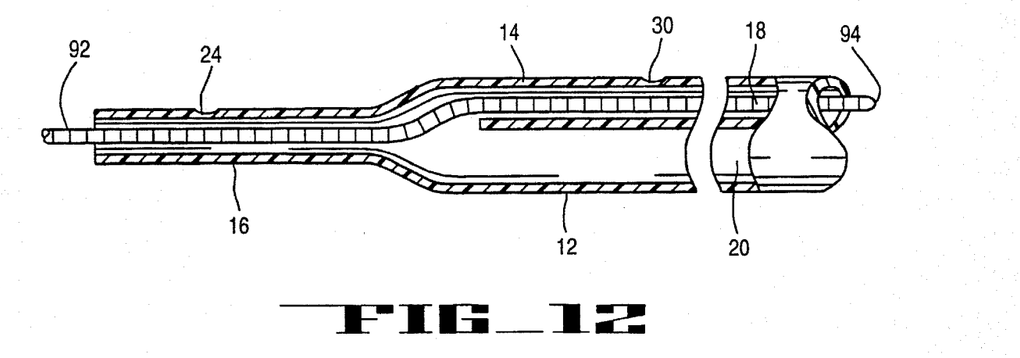

Referring now to FIGS. 8–12, an exemplary method for introducing the catheter 28 of FIG. 2 over a guide wire 92 will be described. Although described in the context of the catheter 28 of FIG. 2, the method described hereinafter is equally applicable to each of the embodiments previously described. For purposes of clarity, however, only reference to catheter 28 will be made. Initially, a proximal end 94 of the guide wire 92 is inserted through the distal end 26 of catheter body 12 and into the single lumen 22 as shown in FIG. 8. Upon reaching the distal guide wire exit port 24, the proximal end 94 of guide wire 92 can be advanced through the distal guide wire exit port as shown in FIG. 9, or can be further advanced through the single lumen 22 and into the proximal region 14, as shown in FIG. 10. If the guide wire 92 is directed through the distal guide wire exit port 24, the catheter 28 will be used as a short lumen rapid exchange catheter as previously described. If the guide wire 92 is further advanced into the proximal region 14, the guide wire 92 can be further advanced into the guide wire lumen 18 where it will approach the proximal guide wire exit port 30. At this point, the guide wire 92 can be further advanced through the proximal guide wire exit port 30 (as shown in FIG. 11) or further through the guide wire lumen 18 until exiting the proximal region 14 as shown in FIG. 12. If the guide wire 92 is directed through the proximal guide wire exit port 30, the catheter 28 will be used as a long lumen rapid exchange catheter as previously described. Alternatively, if the guide wire 92 is directed entirely through the guide wire lumen 18, the catheter 28 will be inserted using a conventional over-the-wire technique.

Figure 13:
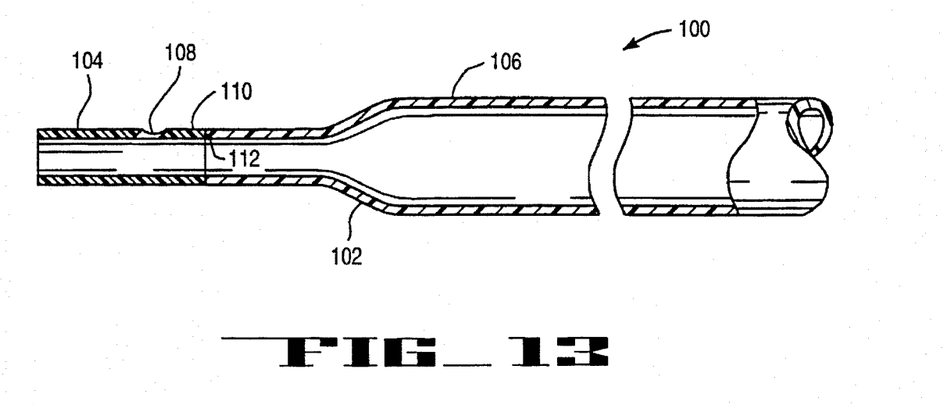
FIGS. 13–14 illustrate a preferential bending scheme for catheters and sheaths having a distal guide wire exit port according to the present invention.
Figure 14:
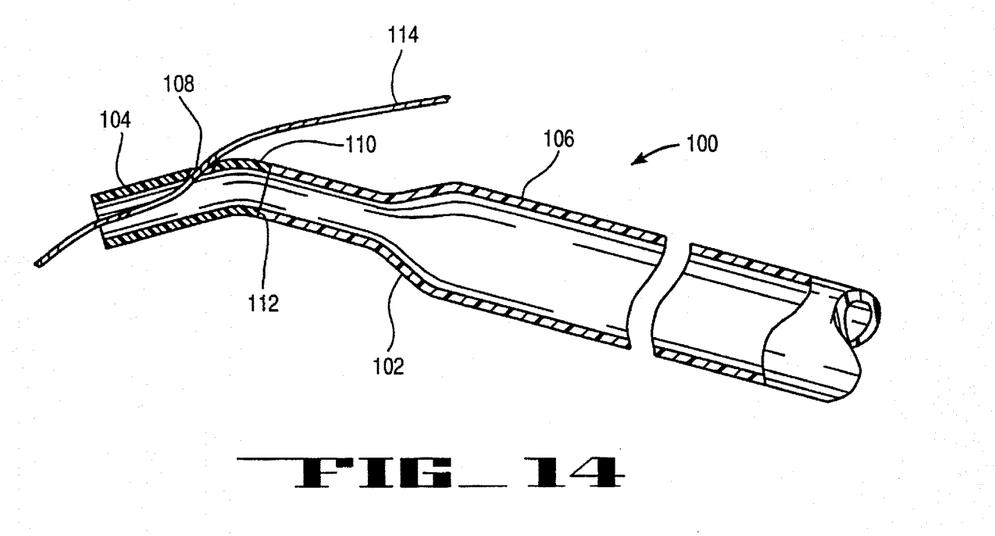

Referring to FIGS. 13 and 14, an exemplary design of a catheter or sheath 100 will be described. The catheter 100 has a catheter body 102 with a distal region 104 and a proximal region 106. In the distal region 104 is a distal guide wire exit port 108. A portion 110 of the distal region 104 that is near the distal guide wire exit port 108 is constructed of a material that is softer than the material used to construct the catheter body 102 just proximal to the distal guide wire exit port 108. Preferably, the material used to construct the soft portion 110 will be low density polyethylene, and materials used to construct the catheter body 102 just proximal to the soft portion 110 include a blend of a low and medium density polyethylene, a blend of a low and high density polyethylene, and the like. The soft and hard materials are preferably joined by fusing the two materials together at a fusion point 112. Preferably, the fusion point 112 will be located about 2 mm to 3 mm from the distal exit port 108. This configuration provides a preferential bending scheme so that when the distal region 104 of the catheter is bent, the catheter body 102 will bend near the distal guide wire exit port 108 to more easily allow a guide wire 114 to exit from the port 108 as shown in FIG. 14.

Although the foregoing invention has been described in some detail by way of illustration and example, for purposes of clarity of understanding, it will be obvious that certain changes and modifications may be practiced within the scope of the appended claims.

What is claimed is:

1. A vascular catheter, comprising:

a catheter body having a proximal end and a distal end, wherein the catheter body has a proximal region having at least one lumen and a first outside diameter and a distal region having a single lumen and a second outside diameter which is less than the first diameter, wherein a distal guide wire exit port is disposed in the distal region of the catheter body within 5 cm of the distal end, the catheter body being formed such that a guidewire may be advanced into the single lumen from the distal end, the catheter body being formed such that a guidewire may be advanced into the single lumen from the distal end of the catheter body and selectively directed through the exit port or advanced further through the catheter body and into the proximal region.

2. A vascular catheter as in claim 1, wherein a proximal guide wire exit port is disposed in the proximal region within 10 cm to 20 cm of a proximal end of the distal region.

3. A vascular catheter as in claim 1, further comprising a transition region near the distal guide wire exit port for assisting in the advancement of the guide wire through the distal guide wire exit port.

4. A vascular catheter as in claim 3, wherein the transition region includes a guide in the single lumen.

5. A vascular catheter as in claim 4, wherein the guide includes an inclined member integrally formed with the catheter body.

6. A vascular catheter as in claim 1, wherein the single lumen has a diameter in the range from 0.6 mm to 1.6 mm.

7. A vascular catheter as in claim 1, wherein at least a portion of the distal region near the distal guide wire exit port is constructed of a material that is softer than material used to construct the catheter body just proximal to the distal guide wire exit port.

8. A vascular catheter as in claim 1, wherein a plurality of infusion ports are disposed in the catheter body proximal to the distal guide wire exit port.

9. A vascular catheter, comprising:

a catheter body having a proximal end and a distal end, wherein the catheter body has a proximal region having at least two lumens and a distal region having a single lumen which is connected to and in communication with both of the lumens in the proximal region, wherein a distal guide wire exit port is disposed in the distal region of the catheter body within 5 cm of the distal end, the catheter body being formed such that a guidewire may be advanced into the single lumen from the distal end of the catheter body and selectively directed through the exit port or advanced further through the catheter body and into the proximal region.

10. A vascular catheter as in claim 9, wherein a proximal guide wire exit port is disposed in the proximal region of the catheter body within 10 cm to 20 cm of a proximal end of the distal region.

11. A vascular catheter as in claim 9, further comprising a transition region near the distal guide wire exit port for assisting in the advancement of the guide wire through the distal guide wire exit port.

12. A vascular catheter as in claim 11, wherein the transition region includes a guide in the single lumen.

13. A vascular catheter as in claim 12, wherein the guide includes an inclined member integrally formed with the catheter body.

14. A vascular catheter as in claim 9, wherein at least a portion of the distal region near the distal guide wire exit port is constructed of a material that is softer than material used to construct the catheter body just proximal to the distal guide wire exit port.

15. A vascular catheter as in claim 10, wherein the single lumen has a diameter in the range from 0.6 mm to 1.6 mm.

16. A vascular catheter as in claim 10, wherein one of the two lumens in the proximal region is a guide wire lumen having a diameter in the range from 0.3 mm to 0.6 mm.

17. A vascular catheter as in claim 16, wherein the proximal guide wire exit port is in communication with the guide wire lumen.

18. A vascular catheter as in claim 9, wherein the distal region has a cross-sectional area which is less than the cross-sectional area of the proximal region.

19. A vascular catheter as in claim 9, wherein a plurality of infusion ports are disposed in the catheter body proximal to the distal guide wire exit port.

20. A method for inserting a catheter over a guide wire, the method comprising:

providing a catheter comprising a catheter body having a proximal end and a distal end, wherein the catheter body has a proximal region having a first diameter and a distal region having a single lumen and a second diameter which is less than the first diameter, wherein a distal guide wire exit port is disposed in the distal region of the catheter body within 5 cm of the distal end; the catheter body being formed such that a guidewire may be advanced into the single lumen from the distal end of the catheter body and selectively directed through the exit port or advanced further through the catheter body and into the proximal region;

introducing the distal end of the catheter body over the guidewire so that the guidewire is within the single lumen;

advancing the distal region of the catheter body over the guide wire; and selectively directing the guide wire (1) through the distal guide wire exit port or (2) into the proximal region of the catheter.

21. The method of claim 20, further comprising directing the guide wire (1) through a proximal guide wire exit port or (2) out of the catheter body through the proximal end.

22. The method of claim 20, further comprising introducing a working element through the proximal region.

23. The method of claim 20, further comprising directing the guide wire through a guide wire lumen in the proximal region.

24. The method of claim 23, further comprising directing a working element through a working lumen in the proximal region.

25. The method of claim 20, further comprising withdrawing the guide wire from the distal end and delivering perfusion through a plurality of perfusion ports disposed in the distal region.

26. The method of claim 20, further comprising bending the catheter body near the distal guide wire exit port to assist in guiding the guide wire through the exit port.

* * * * *